US011278046B2

(12) United States Patent
Kirchen et al.

(10) Patent No.: US 11,278,046 B2
(45) Date of Patent: Mar. 22, 2022

(54) MULTIVITAMIN EXTRUDATES

(71) Applicant: DSM IP ASSETS B.V., Heerlen (NL)

(72) Inventors: Stefanie Kirchen, Kaiseraugst (CH); Alexandra Teleki, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 232 days.

(21) Appl. No.: 15/763,929

(22) PCT Filed: Oct. 6, 2016

(86) PCT No.: PCT/EP2016/073822
§ 371 (c)(1),
(2) Date: Mar. 28, 2018

(87) PCT Pub. No.: WO2017/060320
PCT Pub. Date: Apr. 13, 2017

(65) Prior Publication Data
US 2018/0263270 A1    Sep. 20, 2018

(30) Foreign Application Priority Data

Oct. 7, 2015 (EP) .................................... 15188726

(51) Int. Cl.
| | |
|---|---|
| *A23L 33/155* | (2016.01) |
| *A23K 20/174* | (2016.01) |
| *A23L 29/10* | (2016.01) |
| *A61K 8/67* | (2006.01) |
| *A61K 8/73* | (2006.01) |
| *A23P 10/25* | (2016.01) |
| *A23L 29/212* | (2016.01) |
| *A23L 33/15* | (2016.01) |
| *A61K 9/14* | (2006.01) |
| *A61Q 19/00* | (2006.01) |
| *A61K 8/9794* | (2017.01) |
| *A61K 9/16* | (2006.01) |
| *A23K 40/20* | (2016.01) |

(52) U.S. Cl.
CPC .......... *A23L 33/155* (2016.08); *A23K 20/174* (2016.05); *A23L 29/10* (2016.08); *A23L 29/212* (2016.08); *A23L 33/15* (2016.08); *A23P 10/25* (2016.08); *A61K 8/67* (2013.01); *A61K 8/671* (2013.01); *A61K 8/675* (2013.01); *A61K 8/676* (2013.01); *A61K 8/678* (2013.01); *A61K 8/732* (2013.01); *A61K 8/9794* (2017.08); *A61K 9/146* (2013.01); *A61K 9/16* (2013.01); *A61Q 19/00* (2013.01); *A23K 40/20* (2016.05); *A23V 2002/00* (2013.01); *A23V 2200/02* (2013.01); *A23V 2200/222* (2013.01); *A23V 2250/702* (2013.01); *A23V 2250/705* (2013.01); *A23V 2250/706* (2013.01); *A23V 2250/708* (2013.01); *A23V 2250/7042* (2013.01); *A23V 2250/7044* (2013.01); *A23V 2250/7046* (2013.01); *A23V 2250/7052* (2013.01); *A23V 2250/7054* (2013.01); *A23V 2250/7058* (2013.01); *A23V 2250/712* (2013.01); *A23V 2250/714* (2013.01); *A23V 2250/7106* (2013.01); *A23V 2300/16* (2013.01); *A61K 2800/10* (2013.01); *A61K 2800/522* (2013.01)

(58) Field of Classification Search
CPC .... A23L 33/15; A23L 33/16; A61K 8/67; A61K 9/16
USPC ................ 426/72, 73, 74, 648, 516, 518
See application file for complete search history.

(56) References Cited

U.S. PATENT DOCUMENTS

| | | | |
|---|---|---|---|
| 2,441,409 | A * | 5/1948 | Green |
| 5,290,560 | A | 3/1994 | Autant et al. |
| 6,190,591 | B1 | 2/2001 | Van Lengerich |
| 6,422,135 | B1 * | 7/2002 | Huber et al. |
| 2001/0009679 | A1 | 7/2001 | Chen et al. |
| 2013/0228429 | A1 * | 9/2013 | Henmi |
| 2014/0147501 | A1 * | 5/2014 | Van Lengerich |
| 2014/0228429 | A1 * | 8/2014 | Funda et al. |

FOREIGN PATENT DOCUMENTS

| | | |
|---|---|---|
| CN | 103717085 | 4/2014 |
| DE | 195 04 832 | 8/1996 |
| DE | 195 36 387 | 4/1997 |
| EP | 1 836 902 | 9/2007 |
| JP | 10513477 | 12/1998 |
| JP | 2002511777 | 4/2002 |
| JP | 4230318 | 2/2009 |
| WO | WO 2012/163836 | 12/2012 |
| WO | WO 2014/083065 | 6/2014 |

OTHER PUBLICATIONS

International Search Report for PCT/EP2016/073822, dated Nov. 9, 2016, 6 pages.
Written Opinion of the ISA for PCT/EP2016/073822, dated Nov. 9, 2016, 6 pages.
Bhaskaran et al. "Extrusion Spheronization—A Review", International Journal Of PharmTech Research CODEN (USA): IJPRIF, Oct. 1, 2010, 5 pages.
https://bakerpedia.com/processes/particle-size (Apr. 27, 21).
Hareland, G.A., *Evaluation of Flour Particle Size Distribution by Laser Diffraction, Sieve Analysis and Near-infrared Reflectance Spectroscopy*, Journal of Cereal Science 21 (1994) 183-190.

\* cited by examiner

*Primary Examiner* — Helen F Heggestad
(74) *Attorney, Agent, or Firm* — Nixon & Vanderhye P.C.

(57) ABSTRACT

This invention relates generally to multivitamin extrudates. Their production as well as their use.

9 Claims, No Drawings

MULTIVITAMIN EXTRUDATES

This application is the U.S. national phase of International Application No. PCT/EP2016/073822 filed Oct. 6, 2016, which designated the U.S. and claims priority to EP Patent Application No. 15188726.2 filed Oct. 7, 2015, the entire contents of each of which are hereby incorporated by reference.

This invention relates generally to multivitamin extrudates, their production as well as their use.

Extrusion is a well-known process for the production of many kind of formulations. Extrusion is also used in many kind of technical fields. In fact extrusion is a very versatile process.

Extrusion is a process used to create objects of a fixed cross-sectional profile.

In principle, it can be distinguished between hot and cold and warm extrusion.

Hot extrusion is a hot working process, which means it is done above the material's melting temperature to keep the material from hardening and to make it easier to push the material through the die. Most hot extrusions are done on horizontal hydraulic presses that range from 230 to 11,000 metric tons (pressures range from 30 to 700 MPa).

Cold extrusion is done at room temperature or near room temperature.

Warm extrusion is done above room temperature, but below the melting temperature of the material. The temperatures ranges from 100 to 975° C. It is usually used to achieve the proper balance of required forces, ductility and final extrusion properties.

To formulate fat-soluble vitamins containing formulations, there are also other technologies, such as spray drying, spray chilling etc, which are commonly used.

The goal of the present invention was to find a way to produce multivitamin formulations in an easy and improved way.

It is the goal that these multivitamin formulations can be used as such or in any other composition, which comprises multivitamins.

Nowadays, when for example a multivitamin tablet is produced, a premix of the various vitamins is produced. This is done by mixing together the different vitamins or vitamin formulations in the desired amounts and it is then used like that. Usually each vitamin formulation is produced separately (usually by spray drying). Such commonly practiced way of working needs a lot of handling always connected with a risk of contamination. Furthermore, the handling of powders is usually connected with dust issues.

Now we found a way to deliver a formulation in the form of an extrudate, wherein all the vitamins (which are needed and desired) are present in the amount which is necessary for its application.

With such an extrudate the mixing and the production of the different vitamin formulations is unnecessary.

Additionally, the extrudates of the present invention can comprise a high total amount of the vitamins (at least 8 weight-% (wt-%)), based on the total weight of the extrudate.

Additionally, the extrudates can comprise a mixture of various water-soluble vitamins or a mixture of various oil-soluble vitamins or a mixture of water-soluble and oil-soluble vitamins.

Furthermore, the formulation according to the present invention is free flowing (no dust issues!).

Therefore the present invention relates to an extrudate (E), which comprises at least 8 wt-%, based on the total weight of the extrudate, of more than one water soluble vitamin and/or more than one oil-soluble vitamin.

The distribution of the vitamins in the extrudate is excellent, this means that the ratio (w/w) of the various vitamins is substantially the same in all the extrudates (particles).

The extrudate according to the present invention can have any common form and sizes. This depends a lot for what further composition the extrudates are used. Usually the extrudates according to the present invention are particles with a diameter (of the largest dimension of the particle) of up to 1000 µm.

Preferably the particles have a sphere-like form. When the extrudates are used as such then they are usually larger (up to 1 mm) as when they are used in a formulation (usually 100-600 µm). As stated above the obtained extrudates are in a free flowing form (powder).

The particle size and shape can be controlled by commonly known means, typically by the choice of die shape and diameter.

Furthermore the extrudates according to the present invention can comprise up to 95 wt-%, based on the total weight of the extrudate, of more than one water soluble vitamin and/or more than one oil-soluble vitamin.

Therefore the present invention relates to an extrudate (E1), which is extrudate (E), comprising up to 95 wt-%, based on the total weight of the extrudate, of more than one water soluble vitamin and/or more than one oil-soluble vitamin.

A preferred range is 8 wt-% to 95 wt-%, based on the total weight of the extrudate, of more than one water soluble vitamin and/or more than one oil-soluble vitamin.

Another preferred range is 8 wt-% to 80 wt-%, based on the total weight of the extrudate, of more than one water soluble vitamin and/or more than one oil-soluble vitamin.

Another preferred range is 8 wt-% to 60 wt-%, based on the total weight of the extrudate, of more than one water soluble vitamin and/or more than one oil-soluble vitamin.

Another preferred range is 8 wt-% to 50 wt-%, based on the total weight of the extrudate, of more than one water soluble vitamin and/or more than one oil-soluble vitamin.

Therefore the present invention relates to an extrudate (E2), which is extrudate (E) or (E1), comprising 8 wt-% to 95 wt-%, based on the total weight of the extrudate, of more than one water soluble vitamin and/or more than one oil-soluble vitamin.

Therefore the present invention relates to an extrudate (E3), which is extrudate (E) or (E1), comprising 8 wt-% to 80 wt-%, based on the total weight of the extrudate, of more than one water soluble vitamin and/or more than one oil-soluble vitamin.

Therefore the present invention relates to an extrudate (E4), which is extrudate (E) or (E1), comprising 8 wt-% to 60 wt-%, based on the total weight of the extrudate, of more than one water soluble vitamin and/or more than one oil-soluble vitamin.

Therefore the present invention relates to an extrudate (E5), which is extrudate (E) or (E1), comprising 8 wt-% to 50 wt-%, based on the total weight of the extrudate, of more than one water soluble vitamin and/or more than one oil-soluble vitamin.

Fat soluble vitamins, which are incorporated into the extrudates according to the present invention are vitamin A or its esters (for example vitamin A acetate and vitamin A palmitate), vitamin E or its esters (for example vitamin E acetate), vitamin K (phytomenadione) and vitamin D3 (cholecalciferol).

Water soluble vitamins, which are incorporated into the extrudates according to the present invention are vitamin B1 (thiamine), vitamin B2 (riboflavin), vitamin B3 (niacin, niacinamide), vitamin B5 (pantothenic acid), vitamin B6 (pyridoxine, pyridoxamine, pyridoxal), vitamin B7 (biotin), vitamin B9 (folic acid, folinic acid), vitamin B12 (cyanocobalamin, hydroxycobalamin, methylcobalamin), and vitamin C (ascorbic acid).

Such vitamins are readily available from commercial sources. Also, they may be prepared by conventional methods by a skilled person.

The extrudate according to the present invention comprises more than one vitamin chosen from the group consisting of vitamin A or its esters (for example vitamin A acetate and vitamin A palmitate), vitamin E or its esters (for example vitamin E acetate), vitamin K (phytomenadione) vitamin D3 (cholecalciferol), vitamin B1 (thiamine), vitamin B2 (riboflavin), vitamin B3 (niacin, niacinamide), vitamin B5 (pantothenic acid), vitamin B6 (pyridoxine, pyridoxamine, pyridoxal), vitamin B7 (biotin), vitamin B9 (folic acid, folinic acid), vitamin B12 (cyanocobalamin, hydroxycobalamin, methylcobalamin), and vitamin C (ascorbic acid).

Therefore the present invention relates to an extrudate (E6), which is extrudate (E), (E1), (E2), (E3), (E4) or (E5), comprising more than one vitamin chosen from the group consisting of vitamin A or its esters (for example vitamin A acetate and vitamin A palmitate), vitamin E or its esters (for example vitamin E acetate), vitamin K (phytomenadione) vitamin D3 (cholecalciferol), vitamin B1 (thiamine), vitamin B2 (riboflavin), vitamin B3 (niacin, niacinamide), vitamin B5 (pantothenic acid), vitamin B6 (pyridoxine, pyridoxamine, pyridoxal), vitamin B7 (biotin), vitamin B9 (folic acid, folinic acid), vitamin B12 (cyanocobalamin, hydroxycobalamin, methylcobalamin), and vitamin C (ascorbic acid).

The extrudate according to the present invention can be an extrudate which only comprises water-soluble vitamins (which means that no oil-soluble vitamins are present in the extrudate). In that case the content of vitamins can be very high. Up to 95 wt-%, based on the total weight of the extrudate, of water soluble vitamins is possible and suitable. Preferably up to 60 wt-%, based on the total weight of the extrudate, of water soluble vitamins is preferred. More preferably up to 50 wt-%, based on the total weight of the extrudate, of water soluble vitamins is preferred.

An usual and preferred range is 8-60 wt-%, based on the total weight of the extrudate, of one or more water-soluble vitamins, wherein the extrudate is free from any oil-soluble vitamins.

The water soluble vitamins are chosen from the group consisting of vitamin B1, vitamin B2, vitamin B3, vitamin B5, vitamin B6, vitamin B7, vitamin B9, vitamin B12 and vitamin C. Another usual and preferred range is 8-50 wt-%, based on the total weight of the extrudate, of one or more water-soluble vitamins chosen from the group consisting of vitamin B1, vitamin B2, vitamin B3, vitamin B5, vitamin B6, vitamin B7, vitamin B9, vitamin B12 and vitamin C, wherein the extrudate is free from any oil-soluble vitamins.

The extrudate according to the present invention can be an extrudate which only comprises oil-soluble vitamins (which means that no water-soluble vitamins are present in the extrudate).

Fat soluble vitamins are chosen from the group consisting of vitamin A or its esters, vitamin E or its esters, vitamin K and vitamin D3.

In that case the content of vitamins is not as high as for the water soluble vitamins. Usually up to 40 wt-% of oil soluble vitamins are in the extrudate, Another usual and preferred range is 8-30 wt-%, based on the total weight of the extrudate, of one or more water-soluble vitamins chosen from the group consisting of vitamin A or its esters, vitamin E or its esters, vitamin K and vitamin D3, wherein the extrudate is free from any water-soluble vitamins.

Another usual and preferred range is 8-20 wt-%, based on the total weight of the extrudate, of one or more water-soluble vitamins chosen from the group consisting of vitamin A or its esters, vitamin E or its esters, vitamin K and vitamin D3, wherein the extrudate is free from any water-soluble vitamins.

The extrudate according to the present invention can be an extrudate which comprises a mixture of water-soluble vitamin(s) and oil-soluble vitamin(s).

Therefore the present invention relates to an extrudate (E7), which is extrudate (E), (E1), (E2), (E3), (E4), (E5) or (E6), which only comprises water-soluble vitamins chosen from the group consisting of vitamin B1, vitamin B2, vitamin B3, vitamin B5, vitamin B6, vitamin B7, vitamin B9, vitamin B12, and vitamin C (free of any oil-soluble vitamins).

For these extrudates the content is preferably between 8 wt-% and 60 wt-%, based on the total weight of the extrudate.

For these extrudates the content is preferably between 8 wt-% and 50 wt-%, based on the total weight of the extrudate.

Therefore the present invention relates to an extrudate (E7'), which is extrudate (E7), wherein the content of the water-soluble vitamins, wherein the extrudate is free from any oil-soluble vitamins is up to 95 wt-%, based on the total weight of the extrudate.

Therefore the present invention relates to an extrudate (E7"), which is extrudate (E7), wherein the content of the water-soluble vitamins is from 8-60 wt-%, based on the total weight of the extrudate.

Therefore the present invention relates to an extrudate (E7'''), which is extrudate (E7), wherein the content of the water-soluble vitamins is from 8-50 wt-%, based on the total weight of the extrudate.

Therefore the present invention relates to an extrudate (E8), which is extrudate (E), (E1), (E2), (E3), (E4), (E5) or (E6), which only comprises oil-soluble vitamins chosen from the group consisting of vitamin A or its esters, vitamin E or its esters, vitamin K and vitamin D3 wherein the extrudate is free from any water-soluble vitamins.

Therefore the present invention relates to an extrudate (E8'), which is extrudate (E8), wherein the content of the vitamins is up to 40 wt-%, based on the total weight of the extrudate.

Therefore the present invention relates to an extrudate (E8"), which is extrudate (E8), wherein the content of the vitamins is 8-30 wt-% based on the total weight of the extrudate.

The extrudate according to the present invention comprises at least two vitamins (water- and/or oil-soluble).

Another embodiment of the present invention relates to an extrudate comprising at least three vitamins (water- and/or oil-soluble).

Another embodiment of the present invention relates to an extrudate comprising at least four vitamins (water- and/or oil-soluble).

Therefore the present invention relates to an extrudate (E9), which is extrudate (E), (E1), (E2), (E3), (E4), (E5) or (E6), (E7), (E7'), (E7"), (E7'''), (E8), (E8') or (E8"), wherein the extrudate comprises at least three vitamins.

Therefore the present invention relates to an extrudate (E9'), which is extrudate (E), (E1), (E2), (E3), (E4), (E5), (E6), (E7), (E7'), (E7"), (E7'''), (E8), (E8') or (E8"), wherein the extrudate comprises at least four vitamins.

As stated above the extrudate according to the present invention can be an extrudate which comprises a mixture of water-soluble vitamin(s) and oil-soluble vitamin(s).

Therefore the present invention relates to an extrudate (E10), which is extrudate (E), (E1), (E2), (E3), (E4), (E5), (E6), (E9) or (E9'), which comprises a mixture of at least one water-soluble vitamin and at least one oil-soluble vitamin.

The present invention relates to an extrudate (E10'), which is extrudate (E10), which comprises at least two water-soluble vitamins and at least one oil-soluble vitamin.

The present invention relates to an extrudate (E10"), which is extrudate (E10), which comprises at least three water-soluble vitamins and at least one oil-soluble vitamin.

The present invention relates to an extrudate (E10'''), which is extrudate (E10), which comprises at least two water-soluble vitamins and at least one oil-soluble vitamin.

The present invention relates to an extrudate (E10''''), which is extrudate (E10), which comprises 2, 3, 4, 5, 6, or 7 (different) water-soluble vitamins and 2, 3 or 4 (different) oil-soluble vitamins.

In case oil-soluble vitamins are used to form the extrudates according to the present invention, then the extrudate according to the present invention comprises at least one commonly known and used emulsifier.

It also possible to add at least one emulsifier to a extrudate which comprises water-soluble vitamins only.

The content of at least one emulsifier in the extrudate according to the present invention is between 10-92 wt-%, preferably 15-92 wt-%, more preferably 20-92 wt-%, based on the total weight of the extrudate.

It is clear that the added percentages never exceed 100 and the added percentages for an extrudate are always 100. This requirement is valid for all extrudates described in this patent application.

As stated above at least one emulsifier is used in the process according to the present invention when at least one oil soluble vitamin is used. Any commonly known and used emulsifier can be used. The emulsifier can be chosen depending on the final use of the extrudate afterwards. That means if the extrudate obtained by the process according to the present invention is used in food or feed product, the emulsifier must be food or feed grade.

Suitable emulsifiers are i.e. modified (food) starches, pectin, alginate, carrageenan, furcellaran, chitosan, maltodextrin, dextrin derivatives, celluloses and cellulose derivatives (e.g. cellulose acetate, methyl cellulose, hydroxypropyl methyl cellulose), lignosulfonate, polysaccharide gums (such as gum acacia, gum arabic, flaxseed gum, ghatti gum, tamarind gum and arabinogalactan), gelatine (bovine, fish, pork, poultry), plant proteins (such as are for example peas, soybeans, castor beans, cotton, potatoes, sweet potatoes, manioc, rapeseed, sunflowers, sesame, linseed, safflower, lentils, nuts, wheat, rice, maize, barley, rye, oats, lupin and sorghum), animal proteins including milk or whey proteins, lecithin, polyglycerol ester of fatty acids, monoglycerides of fatty acids, diglycerides of fatty acids, sorbitan ester, propylene glycol (PG) ester and sugar ester (as well as derivatives thereof).

The starches can be modified physically and chemically. Pregelatinized starches are examples of physically modified starches. Acidic modified, oxidized, cross-linked, starch esters, starch ethers and cationic starches are examples of chemically modified starches.

Therefore the present invention relates to an extrudate (E11), which is extrudate (E), (E1), (E2), (E3), (E4), (E5), (E6), (E8), (E8') (E8"), (E9), (E9'), (E10), (E10"), (E10''') or (E10''''), comprising at least one emulsifier.

Therefore the present invention relates to an extrudate (E11'), which is extrudate (E), (E1), (E2), (E3), (E4), (E5), (E6), (E7), (E7'), (E7"). (E7'''), (E7''''), (E8), (E8') (E8"), (E9), (E9'), (E10), (E10"), (E10''') or (E10''''), comprising at least one emulsifier.

Therefore the present invention relates to an extrudate (E11'), which is extrudate (E11) or (E11'), comprising 15-92 wt-% (preferably 20-92 wt-%) of at least one emulsifier, based on the total weight of the extrudate.

As stated above the added percentages never exceed 100 and the added percentages for an extrudate are always 100.

Therefore the present invention relates to an extrudate (E11'''), which is extrudate (E11), (E11') or (E11"), wherein the emulsifier is chosen from the group consisting of modified (food) starches, pectin, alginate, carrageenan, furcellaran, chitosan, maltodextrin, dextrin derivatives, celluloses and cellulose derivatives (e.g. cellulose acetate, methyl cellulose, hydroxypropyl methyl cellulose), lignosulfonate, polysaccharide gums (such as gum acacia, gum arabic, flaxseed gum, ghatti gum, tamarind gum and arabinogalactan), gelatine (bovine, fish, pork, poultry), plant proteins (such as are for example peas, soybeans, castor beans, cotton, potatoes, sweet potatoes, manioc, rapeseed, sunflowers, sesame, linseed, safflower, lentils, nuts, wheat, rice, maize, barley, rye, oats, lupin and sorghum), animal proteins including milk or whey proteins, lecithin, polyglycerol ester of fatty acids, monoglycerides of fatty acids, diglycerides of fatty acids, sorbitan ester, PG ester and sugar ester (as well as derivatives thereof).

It is also possible that the extrudates comprises ingredients (auxiliary agents). Such auxiliary agents can be useful for the extrusion process and/or for the extrudate and/or for the product (or application), wherein the extrudate is used afterwards.

Such auxiliary agents are for example antioxidants (such as ascorbic acid or salts thereof, tocopherol (synthetic or natural); butylated hydroxytoluene (BHT); butylated hydroxyanisole (BHA); propyl gallate; tert. butyl hydroxyquinoline and/or ascorbic acid esters of a fatty acid); ethoxyquin; plasticisers; stabilisers; humectants (such as glycerine, sorbitol, polyethylene glycol); protective colloids; dyes, fragrances; minerals (such as zinc gluconate, copper (II) gluconate, postassium iodide, sodium selenite, ferrous fumarate, tri-calcium phosphate, ferrous sulfate, zinc sulfate); fillers (such as for example micro crystalline cellulose) and buffers.

These auxiliary agents are added optionally. When added then the amount of the auxiliary agents goes from 0.1 to 92 wt-%, based on the total weight of the extrudate. (when used preferably 20-60 wt-%).

Therefore the present invention relates to an extrudate (E12), which is extrudate (E), (E1), (E2), (E3), (E4), (E5), (E6), (E7), (E7'), (E7"). (E7'''), (E7''''), (E8), (E8') (E8"), (E9), (E9'), (E10), (E10"), (E10'''), (E10''''), (E11), (E10") or (E11") comprising at least one auxiliary agent.

Therefore the present invention relates to an extrudate (E12'), which is extrudate (E12), which comprises 0.1 to 92 wt-%, based on the total weight of the extrudate, of at least one auxiliary agent.

Therefore the present invention relates to an extrudate (E12"), which is extrudate (E12), which comprises 20 to 60 wt-%, based on the total weight of the extrudate, of at least one auxiliary agent.

The extrudates (E1), (E2), (E3), (E4), (E5), (E6), (E7), (E7'), (E7"). (E7'''), (E7''''), (E8), (E8') (E8"), (E9), (E9'), (E10), (E10"), (E10'''), (E10''''), (E11), (E10"), (E11"), (E12), (E12') and (E12") according to the present invention (are produced by using commonly known extrusion conditions as well as devices.

The temperature inside the extruder is usually between 20 and 220° C. Preferably the temperature of extrudates exiting the extruder is <100° C. The total residence time for the ingredients in the extruder is usually between 1 and 400 s.

The amount of shear of the extrusion process according to the present invention is usually 200 to 80000 units.

Furthermore, it is also possible to pump inert gas through the extruder. The inert gas is usually pumped in at the entrance of the extruder. But it could also be pumped in at any stage of the extrusion process (also though several inlets at different locations). Inert gas can be helpful to protect sensible ingredients.

The extruder comprises usually one or more screw shafts on which various conveying or kneading type screw elements are mounted.

The material is transported by these elements through the extruder (optionally under pressure and elevated temperature). At the end (exit) of the extruder there can be a die through which the extruded material is pressed. Afterwards the extruded material is dried and cut (or also vice versa). The extruder can have several inlets through which the material can be added.

At the end of the extrusion process (when the extrusion strand leaves the extruder), the strand will be cut, formed and dried to obtain the particles in the desired shape and size.

The extrudates according to the present invention can be used as such as well as in other formulations.

When the extrudates are used as such they can be consumed by the consumer (human and/or animal) as such or mixed together with other ingredients. The extrudates according to the present invention can also be used in food, feed, pharma and/or personal care formulations, as well as in premixes for food, feed, pharma and/or personal care formulations.

The present invention also relates to the use of least one extrudate (E1), (E2), (E3), (E4), (E5), (E6), (E7), (E7'), (E7"). (E7'''), (E7''''), (E8), (E8') (E8"), (E9), (E9'), (E10), (E10"), (E10'''), (E10''''), (E11), (E10"), (E11"), (E12), (E12') or (E12") as a nutritional composition.

The present invention also relates to the use of least one extrudate (E1), (E2), (E3), (E4), (E5), (E6), (E7), (E7'), (E7"). (E7'''), (E7''''), (E8), (E8') (E8"), (E9), (E9'), (E10), (E10"), (E10'''), (E10''''), (E11), (E10"), (E11"), (E12), (E12') and (E12") for the production of food, feed, pharma and/or personal care formulations.

The present invention also relates to a premix comprising at least one (E1), (E2), (E3), (E4), (E5), (E6), (E7), (E7'), (E7"). (E7'''), (E7''''), (E8), (E8') (E8"), (E9), (E9'), (E10), (E10"), (E10'''), (E10''''), (E11), (E10"), (E11"), (E12), (E12') and (E12").

The present invention also relates to food, feed, pharma and/or personal care formulations comprising at least one extrudate (E1), (E2), (E3), (E4), (E5), (E6), (E7), (E7'), (E7"). (E7'''), (E7''''), (E8), (E8') (E8"), (E9), (E9'), (E10), (E10"), (E10'''), (E10''''), (E11), (E10"), (E11"), (E12), (E12') and (E12").

The following examples serve to illustrate the invention. The temperature is given in ° C. and the percentages are always related to the weight.

EXAMPLES

Example 1: Extruded Multicomponent Particle Comprising all B Vitamins

This example describes the production of solid, extruded particles comprising all B vitamins (thiamine, riboflavin, pyridoxine, niacin, folic acid and cobalamin). The powder premix containing the B vitamins as well as wheat starch and durum wheat semolina as carrier materials was gravimetrically fed (Brabender Technologie) into the first barrel of a laboratory-scale co-rotating twin screw extruder (Thermo Fisher Scientific, HAAKE Polylab OS with PTW16/40 OS twin screw extruder). The extruder consisted of 10 (electrically heated and water-cooled) barrels and a die head (12 or 21×0 0.5 mm) with a screw diameter of 16 mm and a length to diameter ratio of 40. Demineralized water was injected into the second barrel. The temperature of barrels 2-10 as well as the die head was set to 20° C. The powder premix was fed at 500 g/h and 60 g/h water was added. The extrudate strands containing the B vitamins were directly die-face cut by two rotating knives at the die head. After die-face cutting the solid particles were dried in a laboratory-scale fluid bed drier (Retsch TG 200) for 60 minutes at 50° C. to obtain a final water content of 6 wt %.

The content of the dry extrudate particles is shown in Table 1. The Vitamin B2-5-phosphate content was measured by HPLC of the freshly produced extrudate and a recovery of 93% was found.

TABLE 1

Composition of dry extrudate containing all B vitamins.

| Ingredient | Content, wt % in dry extrudate |
|---|---|
| Thiamine mononitrate (B1) | 0.829 |
| Riboflavin 5'-phosphate sodium (B2) | 0.96 |
| Pyridoxine hydrochloride (B6) | 0.74 |
| Niacinamide (B3) | 7.28 |
| Folic Acid (B9) | 0.19 |
| Vitamin B12 Crystalline | 0.001 |
| Wheat starch | 45.00 |
| Durum wheat semolina | 45.00 |

Example 2: Extruded Multicomponent Particle Comprising Oil- and Water-Soluble Vitamins This example describes the production of solid, extruded particles comprising oil- (Vitamin A acetate, Vitamin D3, Vitamin E acetate) and water-soluble (Vitamin C, thiamine, riboflavin, pyridoxine, niacin, folic acid and cobalamin) vitamins. The production of solid, extruded particles comprising emulsified oil-soluble vitamins as well as water-soluble vitamins was conducted on the laboratory-scale co-rotating twin screw extruder described in Example 1. The emulsifier (modified food starch) as well as the filler (microcrystalline cellulose) were premixed with the water-soluble vitamins as shown in Table 2. This powder premix was gravimetrically fed into the first barrel of the twin screw extruder. Demineralized water was injected into the second barrel. The temperature of barrels 2-10 as well as the die head was set to 50° C. The oil-soluble vitamins Vitamin A acetate, Vitamin D3 crystalline, d,l-alpha-tocopheryl acetate (optionally with added antioxidant such as d,l-alpha tocopherol or butylated hydroxytoluene (BHT)) were molten and premixed at 70° C. (Table 3). This oily melt was injected into barrel 5 and mixed with the other components in the downstream barrels. The powder premix was fed at 750 g/h, the oily premix at 40 g/h and 210 g/h water was added. The extrudate strands containing the oil- and water-soluble vitamins were collected, let to cool down to room temperature and subsequently cut by a pelletizer (Thermo Fisher Scientific). The cut, solid particles were dried in a laboratory-scale fluid bed drier (Retsch TG 200) for 60 minutes at 50° C. to obtain a final water content of 5 wt %.

TABLE 2

Composition of powder premix for extrusion of water- and oil-soluble vitamins.

| Ingredient | Content, wt % in powder premix |
| --- | --- |
| Thiamine mononitrate (B1) | 0.51 |
| Riboflavin 5'-phosphate sodium (B2) | 0.61 |
| Pyridoxine hydrochloride (B6) | 0.47 |
| Niacinamide (B3) | 4.61 |
| Folic Acid (B9) | 0.12 |
| Vitamin B12 Crystalline | 0.001 |
| Ascorbic acid fine powder (C) | 20.39 |
| Modified food starch | 29.32 |
| Microcrystalline cellulose | 43.969 |

TABLE 3

Composition of oily melt for extrusion of water- and oil-soluble vitamins.

| Ingredient | Content, wt % in oily melt |
| --- | --- |
| Vitamin A acetate crystalline | 7.30 |
| Vitamin D3 crystalline | 0.08 |
| d,l-alpha-tocopheryl acetate (E) | 91.62 |
| d,l-alpha-tocopherol | 1.00 |

The content of the dry extrudate particles is shown in Table 4. The Vitamin B2-5-phophate, Vitamin A acetate as well as Vitamin D3 contents were measured by HPLC of the freshly produced extrudate and recoveries of 94%, 89% and 100% were found, respectively.

TABLE 4

Composition of dry extrudate containing oil- and water-soluble vitamins.

| Ingredient | Content, wt % in dry extrudate |
| --- | --- |
| Thiamine mononitrate (B1) | 0.482 |
| Riboflavin 5'-phosphate sodium (B2) | 0.577 |
| Pyridoxine hydrochloride (B6) | 0.445 |
| Niacinamide (B3) | 4.374 |
| Folic Acid (B9) | 0.114 |
| Vitamin B12 Crystalline | 0.001 |
| Ascorbic acid fine powder (C) | 19.35 |
| Modified food starch | 27.82 |
| Microcrystalline cellulose | 41.73 |
| Vitamin A acetate crystalline | 0.373 |
| Vitamin D3 crystalline | 0.004 |
| d,l-alpha-tocopheryl acetate (E) | 4.679 |
| d,l-alpha-tocopherol | 0.051 |

Example 3: Extruded Multicomponent Particle Comprising Oil-Soluble Vitamins

This example describes the production of solid, extruded particles comprising oil-soluble (Vitamin A acetate, Vitamin D3, Vitamin E acetate) vitamins. The production of solid, extruded particles comprising emulsified oil-soluble vitamins was conducted on the laboratory-scale co-rotating twin screw extruder described in Example 1. The emulsifier (modified food starch) as well as the filler (microcrystalline cellulose) were premixed at a ratio 2:3. This powder premix was gravimetrically fed into the first barrel of the twin screw extruder. Demineralized water was injected into the second barrel. The temperature of barrels 2-10 as well as the die head was set to 50° C. The oil-soluble vitamins Vitamin A acetate, Vitamin D3 crystalline, d,l-alpha-tocopheryl acetate (optionally with added antioxidant such as d,l-alpha tocopherol or butylated hydroxytoluene (BHT)) were molten and premixed at 70° C. (Table 5). This oily melt was injected into barrel 5 and mixed with the other components in the downstream barrels. The powder premix was fed at 500 g/h, the oily premix at 73 g/h and 300 g/h water was added. The extrudate strands containing the oil- and water-soluble vitamins were collected and subsequently spheronized in batches of 250 g at 1900 rpm for 15 minutes (Gabler R-250). The spheronized, solid particles were dried in a laboratory-scale fluid bed drier (Retsch TG 200) for 60 minutes at 50° C. to obtain a final water content of 4 wt %.

The content of the dry extrudate particles is shown in Table 6. The Vitamin A acetate as well as Vitamin D3 contents were measured by HPLC of the freshly produced extrudate and recoveries of 88% and 92% were found, respectively.

TABLE 5

Composition of oily melt for extrusion of oil-soluble vitamins.

| Ingredient | Content, wt % in oily melt |
| --- | --- |
| Vitamin A acetate crystalline | 7.30 |
| Vitamin D3 crystalline | 0.08 |
| d,l-alpha-tocopheryl acetate (E) | 91.63 |
| d,l-alpha-tocopherol | 0.99 |

TABLE 6

Composition of dry extrudate containing oil-soluble vitamins.

| Ingredient | Content, wt % in dry extrudate |
| --- | --- |
| Vitamin A acetate crystalline | 0.94 |
| Vitamin D3 crystalline | 0.01 |
| d,l-alpha-tocopheryl acetate (E) | 11.73 |
| d,l-alpha-tocopherol | 0.13 |
| Modified food starch | 34.87 |
| Microcrystalline cellulose | 52.32 |

The invention claimed is:
1. A free-flowing powder of sphere-like particles having a size of 100-600 μm which contain no fat-soluble vitamins, wherein the particles are an extrudate of a composition which consists of:
at least 8 wt. %, based on total weight of the extrudate, of multiple water soluble B vitamins, and
a wheat carrier material consisting of a combination of wheat starch, durum wheat semolina, and optionally at least one auxiliary agent.

2. The free-flowing powder according to claim 1, wherein the multiple water soluble B vitamins are present in an amount of at least 8 wt. % to 95 wt. %, based on the total weight of the extrudate.

3. The free-flowing powder according to claim 1, comprising 8 wt. % to 80 wt. %, based on the total weight of the extrudate, of the multiple water soluble B vitamins.

4. The free-flowing powder according to claim 3, wherein the multiple water soluble B vitamins consists of at least three water soluble B vitamins and the wheat carrier material.

5. The free-flowing powder according to claim 1, wherein the multiple water soluble B vitamins consists of more than one B vitamin selected from the group consisting of vitamin B1, vitamin B2, vitamin B3, vitamin B5, vitamin B6, vitamin B7, vitamin B9 and vitamin B12.

6. The free-flowing powder according to claim 1, wherein the at least one auxiliary agent is selected from the group consisting of antioxidants, butylated hydroxytoluene (BHT), butylated hydroxyanisole (BHA), propyl gallate, tert.butyl hydroxyquinoline, ascorbic acid esters of a fatty acid, ethoxyquin, plasticisers, stabilisers, humectants, protective colloids, dyes, fragrances, minerals, fillers and buffers.

7. The free-flowing powder according to claim 1, wherein the at least one auxiliary agent is present in an amount from 0.1 to 92 wt. %, based on the total weight of the extrudate.

8. The free-flowing powder according to claim 1, wherein the wheat starch and the durum wheat semolina are present in the extrudate in a weight ratio of the wheat starch to the durum wheat semolina of 1:1.

9. Food, feed, pharma and/or personal care formulations or premixes for food, feed, pharma and/or personal care formulations comprising the free-flowing powder according to claim 1.

* * * * *